(12) United States Patent
Takahashi et al.

(10) Patent No.: US 6,743,945 B1
(45) Date of Patent: Jun. 1, 2004

(54) CARBOXYLIC ACID AND AMINO ACID OR AMINO CONDENSATE REACTANTS AND MANUFACTURING METHOD THEREFOR

(75) Inventors: Taro Takahashi, Ibaraki (JP); Junko Tobe, Ibaraki (JP); Akihiro Nakamura, Izumisano (JP); Ryosuke Kiwata, Ibaraki (JP); Hirokazu Maeda, Izumisano (JP)

(73) Assignee: Fuji Oil Co., Ltd., Osaka (JP)

( * ) Notice: Subject to any disclaimer, the term of this patent is extended or adjusted under 35 U.S.C. 154(b) by 0 days.

(21) Appl. No.: 09/490,038

(22) Filed: Jan. 24, 2000

Related U.S. Application Data

(63) Continuation-in-part of application No. PCT/JP98/02448, filed on Jun. 1, 1998.

(51) Int. Cl.[7] .......................... A61K 37/00; A61K 31/70
(52) U.S. Cl. ........................ 562/553; 514/2; 514/23
(58) Field of Search .................. 562/553; 514/2, 514/23

(56) References Cited

U.S. PATENT DOCUMENTS

| | | | |
|---|---|---|---|
| 3,716,380 A | * | 2/1973 | Van Pottelsberghe De La Potterie ............ 426/533 |
| 4,032,676 A | * | 6/1977 | Heins et al. ................. 514/526 |
| 5,189,016 A | * | 2/1993 | Madsen et al. ................. 514/2 |

FOREIGN PATENT DOCUMENTS

| | | |
|---|---|---|
| JP | 58-79976 | 5/1983 |
| JP | 59-26130 | 2/1984 |
| JP | 61-234918 | 10/1986 |
| JP | 63-105000 | 5/1988 |
| JP | 7-500312 | 1/1995 |
| JP | 9-500612 | 1/1997 |

OTHER PUBLICATIONS

Goldberg, Schaum's Outline of Theory and Problems of Beginning Chemistry, McGraw–Hill, 2ed. , p. 250.*

"New Lectures on Experimental Chemistry, vol. 14, Synthesis and Reactions of Organic Compounds, Part II (in Japanese)", edited by The Chemical Society of Japan, Maruzen Co., Ltd., Dec. 20, 1977 p. 1136–1137.

* cited by examiner

*Primary Examiner*—D. Margaret Seaman
*Assistant Examiner*—Taylor V Oh
(74) *Attorney, Agent, or Firm*—Shinjyu Global IP

(57) ABSTRACT

The present invention relates to a method of manufacturing compoundable carboxylic acid and amino acid or amino acid condensate reactants by an extremely simple method that does not use substances toxic to human beings, as well as to carboxylic acid and amino acid or amino acid condensate reactants manufactured according to the method. In the present invention, carboxylic acid and amino acid or amino acid condensate reactants are manufactured by mixing carboxylic acids and amino acids or amino-acid condensates under an aqueous system and heating to 100° C. or more, less than 180° C. without vaporizing the water away.

4 Claims, 1 Drawing Sheet

CARBOXYLIC ACID AND AMINO ACID OR AMINO CONDENSATE REACTANTS AND MANUFACTURING METHOD THEREFOR

This is a continuation in part of International Application PCT/JP98/02418, with an international filing date of Jun. 1, 1998.

TECHNICAL FIELD

The present invention relates to carboxylic acid and amino acid or amino acid condensate reactants and manufacturing methods therefor.

In particular, it relates to a method of manufacturing compoundable carboxylic acid and amino acid or amino acid condensate reactants by an extremely simple method that does not use substances toxic to human beings, as well as to carboxylic acid and amino acid or amino acid condensate reactants manufactured according to the method.

BACKGROUND ART

Various studies have been conducted on the reaction of carboxylic acids with amines. In reactions of this type richly reactive substances such as carbonic chloride and acid anhydrides are generally utilized as raw materials. Carbodiimides, though, are used as catalysts, and the reaction products as such are not useful in food products due to safety demands.

As mentioned above, very richly reactive substances and catalysts are used as raw materials in carboxylic acid and amine reactions. Situations arise, moreover, wherein substances toxic to the human body have to be used. Scrupulous care in handling is therefore necessary. Furthermore, because the reactions between carboxyl groups among carboxylic acids, and amino groups among amines are dehydration reactions, in reality there have been no aquatic reactions; hardly any working examples have been reported.

Given the foregoing, there has been no technique sufficient for forming simply and in a short time carboxylic acid and amino acid or amino acid condensate reaction compounds that can be employed in food product applications.

DISCLOSURE OF THE INVENTION

As a result of concerted investigation regarding the above-noted issues, the present inventors, realizing that carboxylic acid and amino acid or amino acid condensate reaction compounds have conventionally not been practicable, gained the knowledge that by a very simple method of mixing in water and heating to 100° C. or more, less than 180° C. without vaporizing the water away, carboxylic acid and amino acid or amino acid condensate reaction compounds can be efficiently and moreover readily formed.

Namely, the present invention is a way of manufacturing carboxylic acid and amino acid or amino acid condensate reaction compounds, and a surfactant manufacturing method, characterized in mixing carboxylic acid and amino acid or amino acid condensates under an aqueous system aid heating to 100° C. or more, less than 180° C. without vaporizing the water away, as well as carboxylic acid and amino acid or amino acid condensate reaction compounds and surfactants manufactured according to the method.

BEST MODE FOR IMPLEMENTING THE INVENTION

Figure 1:
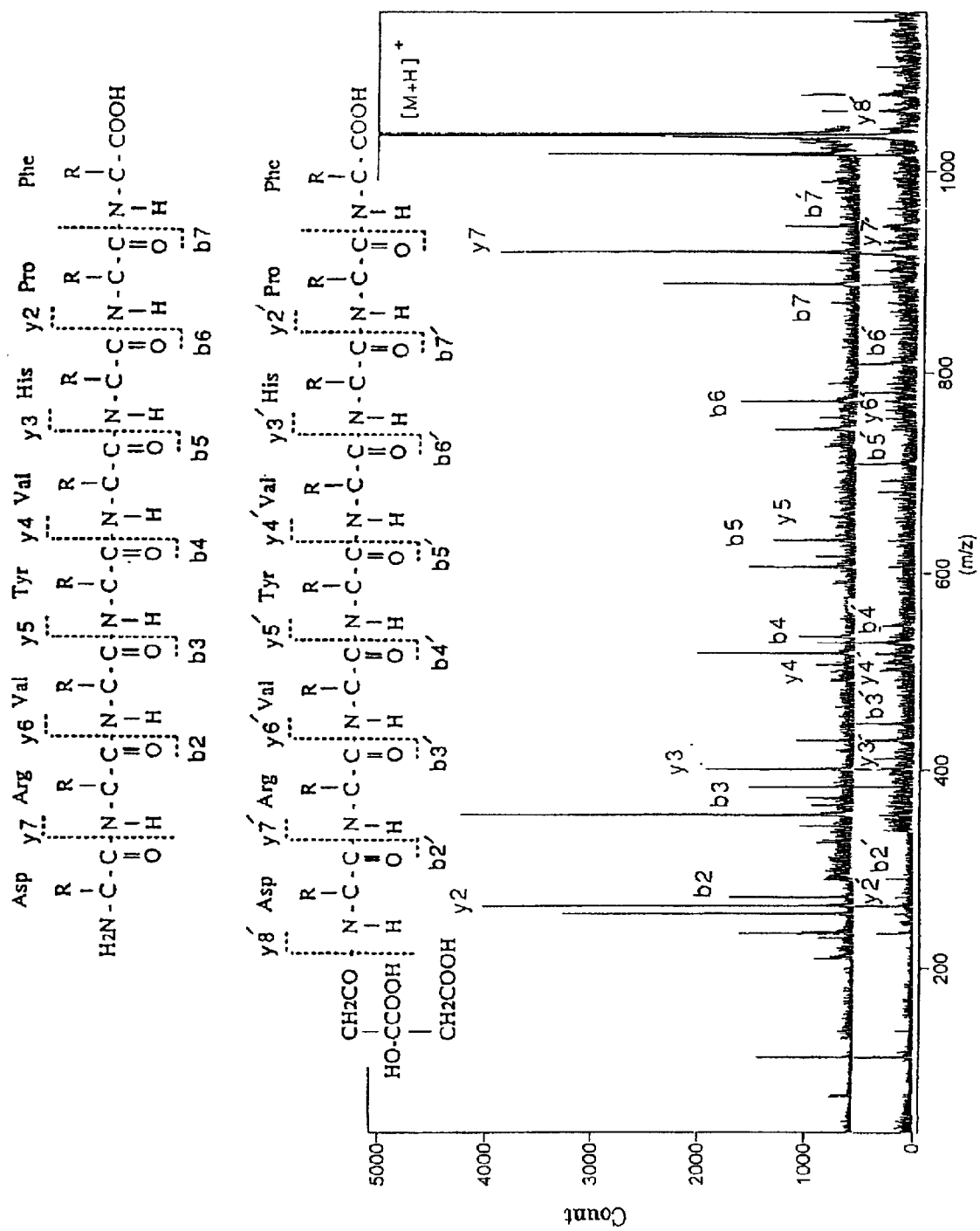
FIG. 1 is a mass spectral analysis of angiotensin II, wherein the y and b series signify a pre-reaction spectrogram, and the y' and b' series a post-reaction spectrogram.

The carboxylic acids and amino acids or amino acid condensates utilized in the present invention are soluble in water, may be any that are insoluble, but preferably should be those that are water soluble.

Examples that may be given of such carboxylic acids are: organic acids such as acetic acid, lactic acid, tartaric acid, citric acid, succinic acid and fumaric acid, and organic acid salts thereof; $C_8$–$C_{18}$ saturated or unsaturated straight-chain or branched fatty acids such as caprylic acid, capric acid, lauric acid, palmitic acid, stearic acid, oleic acid and linoleic acid, or their salts; uronic acids such as galacturonic acid, glucuronic acid and mannuronic acid; acidic polysaccharides containing uronic acids, such as pectin and alginic acid; and acidic oligosaccharides containing uronic acids, such as pectin decomposition products and alginic acid decomposition products, and their salts. The carboxylic acids may be alcohols or esters, but preferably are in de-esterified or isolated form.

Meanwhile, examples that may be given of amino acids or amino acid condensates are: the amino acids, or preferably compounds containing peptides or proteins in which two or more amino acids are combined—animal/vegetal proteins such as soy protein, zein, gluten, casein, whey protein, gelatins and egg white albumin—or peptides and amino acids obtained from their decomposition.

To obtain carboxylic acids and amino acids or amino acid condensate reactants by mix-heating carboxylic acids and amino acids or amino acid condensates, suitable proportions for both raw materials are: carboxylic acids: amino acids or amino acid condensates, 100:1 to 1:100; preferably 50:1 to 1:50; more preferably 10:1 to 1:10.

The foregoing carboxylic acids and amino acids or amino acid condensates are supplied to the reaction in an aqueous solution, dispersed in water, in a suspension, in a moist state, or in paste form. Supplying in these forms, which facilitate the handling conditions of the raw material compounds used is satisfactory. An inordinately large amount of water, however, would mean a large reaction container, and efficiency would therefore deteriorate. Conversely, furthermore, a scant water portion would make the fluidity deficient, and diminish workability. Therefore, these conditions preferably are determined beforehand by experimental determination according to the raw materials used. Further, since it is not necessary to vaporize away the water during the reaction, carrying the reaction out in a sealed container is possible.

Moreover, the reaction system pH under an aqueous system is not particularly limited, but wherein the carboxylic acids are in a de-esterified or isolated state the reaction system pH is preferably put to a pH level at which the carboxyl groups have a charge. Here inorganic acids or organic acids used in food-product or cosmetics applications are employed to adjust the pH.

Both raw materials are mixed under an aqueous system and heated. The temperature for heating is 100° C. or more, preferably 105° C. or more, and more preferably should be carried out at 120° C. The reason for this is that the reaction is finished in a short time. At heating temperatures less than 100° C., a long time is necessary for functions in a surfactant capacity, such as emulsifying functions, to be manifested, which is undesirable. As a consequence of heat-elevating temperatures, the reaction is done in a short time; but temperatures that are quite too high will exert a bad effect on the flavors and hue. Therefore, the temperature it takes to heat is preferably determined beforehand by experimental determination. Concretely, carrying out the reaction at less than 180° C., preferably less than 150° C. is suitable.

Also, since the reaction is carried out under an aqueous system at temperatures that surpass 100° C., all heating for the reaction should be done under pressurization. High temperatures necessitate high-pressure withstanding containers and devices, and the heating temperature has to be considered from this standpoint also.

The following illustrates a manufacturing method of the present invention by examples.

The raw material compounds are put into an aqueous-solution, water-dispersion, suspension, wetted, or paste form and reacted by heating under pressurization at 100° C. or more, preferably 105° C. or more, and more preferably 120° C. or more. This reaction produces carboxylic acid and amino acid, or amino acid condensate, reaction compounds—compounds in which the chemical bonds specifically are by the N-terminals of amino acids or amino acid condensates acid-amide binding with the carboxylic acids. The reactants that contain said reaction compounds can be used as is, or dried, concentrated, or in a form in which insoluble matter has been removed. Also, a preferable mode for said reactants is, after fractionating and further neutralizing the still water-soluble components, purification by carrying out a dialysis process, activated carbon treatment, resin adsorption process, or alcohol precipitation process to remove inorganic salts, hydrophobic substances, or low-molecular substances.

Carboxylic acid and amino acid, or amino acid condensate, reaction compounds in the present invention have novel properties that differ from the pre-reaction carboxylic acids and amino acids or amino acid condensates individually, or from their mere mixtures. For example, properties are manifested that would not be apparent with pre-reaction carboxylic acids and amino acids or amino acid condensates individually, such as emulsifying power, emulsifying stabilization action, ability to improve material characteristics of wheat flour products, dispersion stabilizing action, foaming power, and foam-stabilizing action.

Embodiments

The following explains the present invention according to embodied examples. The present invention is not limited by the examples illustrated. Also, in the present embodiments, "parts" and "%" each signify standard weights.

Experiments

Heating was carried out for ninety minutes on 5 mg of angiotensin II dissolved in 50 $\mu$l of a 100 mM sodium citrate-HCl buffer solution (pH 5.0). The reaction-formed product that arose after heating was separated by reverse-phase HPLC and the reaction compound was recovered. Next, by carrying out mass spectral analysis on the recovered reaction compound as well as the angiotensin II that was the reaction raw material, structural differences in the two compounds were identified. As indicated in the FIG. 1 results, from the outcome of the mass spectral analysis, it can be confirmed that the citric acid that was contained in the buffer solution amide-bound to the N-terminals of angiotensin II.

Further, carboxylic acids and amino acid condensates in the combinations and conditions indicated in Table 1 below were reacted and the presence/absence of reaction compound formations was verified. Also, after recovering the reactants into 10% solution, the formation of reaction compounds was confirmed, taking changed properties (demonstration of emulsifying action) in the reactants as an indicator, by observing the state of the emulsifying substances conditioned by adding an equal volume of soybean oil and emulsifying at 1000 rpm using an homogenizing mixer.

TABLE 1

Combinations, Reaction Conditions and Reactant Presence/Absence Verification Results

| Experiment No. | Carboxylic Acid (parts) | Amino Acid or Its Condensate (parts) | Reaction Conditions ° C. | Time | pH (pre) | pH (post) | Emulsifying Status |
|---|---|---|---|---|---|---|---|
| 1 | Pectin 5 | Soy Protein 1 | 80 | 2 | 6.0 | 4.7 | No Emulsification |
| 2 | Pectin 5 | Soy Protein 1 | 95 | 2 | 6.0 | 4.7 | No Emulsification |
| 3 | Pectin 5 | Soy Protein 1 | 105 | 2 | 6.0 | 4.7 | Slightly Hydrophobic |
| 4 | Pectin 5 | Soy Protein 1 | 120 | 0.5 | 6.0 | 4.7 | Satisfactory |
| 5 | Pectin 5 |  | 120 | 0.5 | 6.0 | 4.7 | No Emulsification |
| 6 |  | Soy Protein 1 | 120 | 0.5 | 6.0 | 5.5 | No Emulsification |
| 7* | Pectin 5 | Soy Protein 1 | 120 | 0.5 | 6.0 |  | No Emulsification |
| 8 | Citric Acid 1 | Soy Protein 20 | 120 | 0.5 | 3.0 | 3.3 | Satisfactory |

TABLE 1-continued

Combinations, Reaction Conditions and Reactant Presence/Absence Verification Results

| Experiment No. | Carboxylic Acid (parts) | Amino Acid or Its Condensate (parts) | Reaction Conditions | | | | Emulsifying Status |
|---|---|---|---|---|---|---|---|
| | | | °C. | Time | pH (pre) | pH (post) | |
| 9 | Sodium Laurate 1 | Soy Peptide 3 | 120 | 0.5 | 8.0 | 8.0 | Satisfactory |
| 10 | Pectin 1 | Casein 5 | 120 | 0.5 | 5.0 | 4.8 | Satisfactory |
| 11 | Pectin 20 | Soy Protein 1 | 120 | 0.5 | 5.0 | 4.4 | Satisfactory |
| 12 | Sodium Laurate 1 | Casein Peptide 10 | 120 | 0.5 | 8.0 | 8.0 | Satisfactory |

In the table, carboxylic acid, amino acid or, amino acid condensate parts are weight proportions in the combinations, which were reacted adding the remaining water to make 100 parts. Further, in the reaction conditions, "pH (pre)" and "pH (post)" signify the pre-reaction and post-reaction change in pH. Also, for Experiment 7, the carboxylic acid and amino acid condensate were mixed after heating separately. As Table 1 above shows, wherein the carboxylic acids, amino acids or amino acid condensates were heated to less than 100° C. after mixing in water, demonstration of emulsifying action by the reactants was not observed even after heating 2 hours (Experiment Nos. 1–2). Further, demonstration of emulsifying action by the reactants also was not observed in heating each of the carboxylic acids, amino acids or amino acid condensates individually at 120° C. (Experiment Nos. 5–6). Moreover, after heating each of the carboxylic acids, amino acids or amino acid condensates individually at 120° C. and mixing them, demonstration of emulsifying action also was not observed (Experiment No. 7).

On the other hand, by heating the carboxylic acids, amino acids or amino acid condensates at 100° C. or more after mixing in water, carboxylic acid, amino acid or amino acid condensate reaction compounds were formed; only in the individual raw materials heated separately was it confirmed anew that emulsifying action was not demonstrated (Experiment Nos. 3–4, and Experiment Nos. 8–12).

Embodiment 1

500 parts pectin and 100 parts soy protein ("FujiPro-E, "Fuji Seiyu Ltd., mfr.) were dissolved in 5400 parts warm water, after which the pH was adjusted to 5.0; a pectin-soy protein reactant was obtained by heating 2 hours at 105° C.

TABLE 2

Combination of Ingredients for Coffee Whitener

| Ingredients Combined | Weight Parts |
|---|---|
| Reactant | 5.0 |
| Water | 75.0 |
| Refined Palm Oil | 20.0 |
| Milk Flavoring | 0.1 |

Coffee whitener was manufactured as below using this reactant, according to the recipe indicated in the above-noted Table 2.

(1) Add 5 parts reactant to 75 parts room-temperature, water, and stir-mix.
(2) Raise the temperature to 70° C. of 20 parts refined palm oil to which 0.1 parts milk flavoring has been added.
(3) Raise the temperature to 70° C. of the reactant solution prepared in (1); add the fatty oil part prepared in (2). After preliminary emulsification in a homogenizing mixer, a main emulsifying process was carried out using a homogenizer at 150 kgf/cm$^2$; and a coffee whitener was manufactured after recovering into a container and cooling.

An accordingly manufactured coffee whitener showed stable emulsification—neither aggregation of emulsifying particles nor separation of the oil portion could be recognized; satisfactory quality was maintained even after preserving for a month. Further, when added to regular coffee (80° C., pH 5.3) containing 5% sugar, no feathering or like demulsification arose, verifying that it has heat resistance and acid resistance. Moreover, it was added to regular coffee (pH adjusted to 6.8 with sodium bicarbonate) containing 5% sugar, which was retorting-sterilized for 15 minutes at 121° C., but no oil portion separation or like demulsification arose, verifying that it had retorting resistance.

Embodiment 2

500 parts pectin and 100 parts soy protein were. dissolved in 5400 parts warm water, after which the pH was adjusted to 5.0; a pectin-soy protein reactant was obtained by heating 30 minutes at 120° C.

TABLE 3

Combination of Ingredients for Sponge Cake

| Ingredients Combined | Weight Parts |
|---|---|
| Whole Eggs | 100 |
| Sugar | 100 |
| Weak Flour | 100 |
| Water | 35 |
| Emulsifying Fatty Oil | 15 |
| Baking Powder | 2 |
| Reactant | 1 |

Sponge cake was prepared as follows using this reactant, according to the recipe indicated in the above-noted Table 3.

(1) Mix 100 parts whole eggs with 100 parts sugar.
(2) Mix 1 part reaction compound with 100 parts weak flour.
(3) Add emulsifying fatty oil, water, the powder mix from (2) to the whole egg and sugar mixture prepared in (1), and whip to 0.4 final specific gravity.
(4) Pour the batter into a mold and bake for 20 minutes at 170° C.

An accordingly manufactured sponge cake had a fine, smooth internal texture and satisfactorily moist feel. Further, the sponge cake preserved 7 days within an airtight container at 20° C., and yet as shown in Table4 below, comparison with a counterpart verified that deterioration in quality was restrained. Here, Comparative Example 1 is a sponge cake manufactured without adding the reactant, but otherwise by the same recipe.

TABLE 4

Change in Stiffness for Preserved Sponge Cake

| | How Long Preserved (Days) | Stiffness* (g/cm$^2$) | Water Portion (%) |
|---|---|---|---|
| Embodiment 2 | 0 | 45.2 | 35.4 |
| | 7 | 80.5 | 30.8 |
| Comparative Example 1 | 0 | 48.1 | 35.5 |
| | 7 | 122.0 | 30.2 |

*Stiffness (g/cm$^2$) is a value by which stress when the sample is compressed to ⅔ is measured utilizing a rheometer (Fudo Kogyo Ltd., infr.) employing a 40 mm dia. plunger at a table speed of 50 mm/min.

Embodiment 3

500 parts sodium alginate and 100 parts soy protein were dissolved in 5400 parts warm water, after which the pH was adjusted to 5.0; an alginic acid-soy protein reactant was obtained by heating 30 minutes at 120° C.

TABLE 5

Combination of Ingredients for Meringue Confection

| Ingredients Combined | Weight Parts |
|---|---|
| Egg Whites | 300 |
| Granulated Sugar | 180 |
| Wheat Starch | 15 |
| Cocoa Powder | 6 |
| Reactant | 4 |

A meringue confection was manufactured as follows using this reactant, according to the recipe indicated in the above-noted Table 5.
(1) Powder-mix so as to keep from clumping 180 parts granulated sugar, 15 parts wheat starch, 6 parts cocoa powder and 4 parts reactant.
(2) Add the egg whites to the mixed powder prepared in (1) and whip to 0.25 final specific gravity.
(3) After whipping, squeeze out at about 1 g and bake 30 minutes at 135° C.

Accordingly manufactured meringue confections exhibited stable foaming, change in state over time during the squeezing-out work was slight, and the texture of the individual meringue confections was stable. Further, almost no constitutional breakdown due to baking was recognized, and the post-baking texture exhibited a fine, satisfactory condition.

Embodiment 4

5 parts succinic acid and 100 parts soy protein were dissolved in 450 parts warm water, after which the pH was adjusted to 6.0; a succinic acid-soy protein reactant was obtained by heating 30 minutes at 120° C. With regard to solubility of the reactant a solubility comparison was made with a sample in which the pH was adjusted to 6.0 without adding succinic acid, and which was heated 30 minutes at 120° C.

After suspending the samples in water, the pH of the solutions was adjusted to 4.5, following which centrifugation was carried out for 20 minutes. The results of measuring the volume of proteinaceous nitrogen remaining in the supernatant—85.8% was dissolved in the succinic acid-soy protein reactant, versus 8.5% in the sample in which only the soy protein was heated—verified that in the weak-acid pH range the solubility was high, resulting in improved solubility.

Embodiment 5

1000 parts Onshu orange peel and 100 parts soy protein were suspended in 4900 parts warm water, after which the pH was adjusted to 4.0; heating 30 minutes at 120° C., reactant preparation and extraction were carried out simultaneously. Following the heat reaction, the solubilized reactant was recovered by centrifuging after cooling to room temperature. When an emulsifying operation likewise as with the experimental examples was carried out using this reactant, a satisfactory emulsifying substance of 0.4$\mu$ emulsifying particulates was obtained, and the formation of a reaction compound was confirmed.

Embodiment 6

1000 parts beet grain and 100 parts soy protein were suspended in 4900 parts warm water, after which the pH was adjusted to 5.0; heating 30 minutes at 120° C., reactant preparation and extraction were carried out simultaneously. Following the heat reaction, the solubilized reactant was recovered by centrifuging after cooling to room temperature. When an emulsifying operation likewise as with the experimental examples was carried out using this reactant, a satisfactory emulsifying substance of 0.5$\mu$ emulsifying particulates was obtained, and the formation of a reaction compound was confirmed.

Comparative Example 2

1000 parts Onshu orange peel and 100 parts soy protein were suspended in 4900 parts warm water, after which the pH was adjusted to 4.0; heating 2 hours at 80° C., reactant preparation and extraction were carried out simultaneously. Following the heat reaction, the solubilized extract was recovered by centrifuging after cooling to room temperature. When an emulsifying operation likewise as with the experimental examples was carried out using this extract, it did not emulsify at all.

Embodiment 7

10 parts sodium stearate and 100 gelatin peptide were dissolved in 140 parts warm water, after which the pH was adjusted to 9.0; a stearic acid-gelatin peptide reactant was obtained by heating 30 minutes at 120° C. Shampoo was prepared using this reactant, according to the recipe indicated in Table 6 below.

TABLE 6

Combination of Ingredients for Shampoo

| Ingredients Combined | Weight Parts |
| --- | --- |
| Polyoxyethylene (2,5) sodium lauryl sulfate | 20.0 |
| Lauryl diethanolamide | 3.0 |
| Reactant | 1.0 |
| Water | 76.0 |

A shampoo prepared as noted above exhibited stable lathering and the foam texture was stable. Further, the condition of the hair after shampooing was good, and combing was smooth.

Industrial Applicability

By mixing carboxylic acid and amino acid or amino acid condensates and afterwards heating to 100° C. or more within water, as in the foregoing, carboxylic acid and amino acid or amino acid condensate reactants can be readily obtained without using substances toxic to the human body.

The reactants concerned are endowed with improved solubility, and satisfactory emulsifying power and foaming strength, which are properties that differ from the individual pre-reaction compounds. They can be used in the chemical synthetic products field in food items and cosmetics.

What is claimed is:

1. A method for manufacturing carboxylic acid and amino acid or ammo acid condensate reaction products, comprising the steps of:

mixing, in an aqueous system, at least one carboxylic acid selected from the group consisting of acetic acid, lactic acid, tartaric acid, citric acid, succinic acid, fumaric acid, caprylic acid, capric acid, lauric acid, palmitic acid, stearic acid, oleic acid, linoleic acid, pectin, pectin decomposition products, alginic acid, alginic acid decomposition products, and sodium or potassium salts thereof with at least one amino acid or anino acid condensate selected from the group consisting of soy protein, zein gluten, casein, whey protein, gelatin, and egg white albumin, wherein the carboxylic acid is mixed with the amino acid or amino acid condensate at a ratio between 50:1 and 1:50; and heating the mixture in an absence of a catalyst to a temperature greater than 105° C. in a closed container capable of withstanding the pressure generated thereby until a carboxylic acid and amino acid or amino acid condensate reaction product is produced.

2. The method for manufacturing carboxylic acid and amino acid or amino acid condensate reaction products according to claim 1, wherein N-terminals of the amino acid or amino acid condensate are acid amide bound with the carboxylic acid after reaction.

3. The method for manufacturing carboxylic acid and amino acid or amino acid condensate reaction products according to claim 1, wherein the carboxylic acid is mixed with the amino acid or amino acid condensate at a ratio between 10:1 to 1:10.

4. The method for manufacturing carboxylic acid and amino acid or amino acid condensate reaction products according to claim 1, wherein the mixture is located to a temperature as high as 120° C.

* * * * *